US012363803B2

(12) United States Patent
Horrod et al.

(10) Patent No.: US 12,363,803 B2
(45) Date of Patent: Jul. 15, 2025

(54) APPARATUS FOR HEATING SMOKABLE MATERIAL

(71) Applicant: Nicoventures Trading Limited, London (GB)

(72) Inventors: Martin Daniel Horrod, Cambridge (GB); Julian Darryn White, Cambridge (GB); Walid Abi Aoun, London (GB); Patrick Moloney, London (GB)

(73) Assignee: NICOVENTURES TRADING LIMITED, London (GB)

( * ) Notice: Subject to any disclaimer, the term of this patent is extended or adjusted under 35 U.S.C. 154(b) by 0 days.

(21) Appl. No.: 18/640,477

(22) Filed: Apr. 19, 2024

(65) Prior Publication Data

US 2024/0268002 A1    Aug. 8, 2024

Related U.S. Application Data

(63) Continuation of application No. 17/858,888, filed on Jul. 6, 2022, now Pat. No. 12,069,790, which is a
(Continued)

(30) Foreign Application Priority Data

Jan. 17, 2017   (GB) ...................... 1700812

(51) Int. Cl.
*H05B 6/10*    (2006.01)
*A24D 1/20*    (2020.01)
(Continued)

(52) U.S. Cl.
CPC ............... *H05B 6/105* (2013.01); *A24D 1/20* (2020.01); *A24F 40/465* (2020.01); *A61M 15/06* (2013.01); *H05B 6/1254* (2013.01); *A24F 40/20* (2020.01)

(58) Field of Classification Search
CPC ......... A24F 40/20; A24F 40/465; A24D 1/20; H05B 6/105; H05B 6/106; H05B 6/108; H05B 6/1254; A61M 15/06
See application file for complete search history.

(56) References Cited

U.S. PATENT DOCUMENTS 2,191,672 A    2/1940  John
2,216,920 A    10/1940  John et al.
(Continued)

FOREIGN PATENT DOCUMENTS

AU    2018209649 B2    2/2021
BR    112019014679 A2   2/2020
(Continued)

OTHER PUBLICATIONS

International Search Report and Written Opinion, PCT Application No. PCT/EP2018/050907, mailed May 3, 2018.
(Continued)

*Primary Examiner* — Marcus E Harcum
(74) *Attorney, Agent, or Firm* — WOMBLE BOND DICKINSON (US) LLP

(57) ABSTRACT

Disclosed is an article for use with an apparatus for heating smokable material to volatilize at least one component of the smokable material. The article includes a carrier having plural thermally-conductive portions, on which are locatable respective discrete quantities of smokable material. Between the portions of the carrier, the carrier is shaped to form a thermal barrier for inhibiting heat conduction from one or more of the portions of the carrier towards another of the portions of the carrier in use.

6 Claims, 6 Drawing Sheets

Related U.S. Application Data continuation of application No. 16/478,724, filed as application No. PCT/EP2018/050907 on Jan. 15, 2018, now Pat. No. 11,503,676.

(51) Int. Cl.
*A24F 40/465* (2020.01)
*A61M 15/06* (2006.01)
*H05B 6/12* (2006.01)
*A24F 40/20* (2020.01)

(56) References Cited

U.S. PATENT DOCUMENTS

| | | |
|---|---|---|
| 3,289,314 A | 12/1966 | Della |
| 3,319,344 A | 5/1967 | Sachsel et al. |
| 4,056,707 A | 11/1977 | Farnam |
| 4,175,334 A | 11/1979 | Gibert |
| 4,503,319 A | 3/1985 | Moritoki et al. |
| 4,622,454 A | 11/1986 | Castille |
| 5,034,721 A | 7/1991 | Benedictus |
| 5,093,894 A | 3/1992 | Deevi et al. |
| 5,285,050 A | 2/1994 | Blackburn |
| 5,387,404 A | 2/1995 | Kutner et al. |
| 5,388,594 A | 2/1995 | Counts et al. |
| 5,479,948 A | 1/1996 | Counts et al. |
| 5,613,505 A | 3/1997 | Campbell et al. |
| 5,692,526 A | 12/1997 | Adams et al. |
| 5,726,421 A | 3/1998 | Fleischhauer et al. |
| 5,730,158 A | 3/1998 | Collins et al. |
| 5,878,752 A | 3/1999 | Adams et al. |
| 5,934,289 A | 8/1999 | Watkins et al. |
| 5,954,979 A | 9/1999 | Counts et al. |
| 6,026,820 A | 2/2000 | Baggett, Jr. et al. |
| 6,188,042 B1 | 2/2001 | Sheen |
| 6,598,607 B2 | 7/2003 | Adiga et al. |
| 6,638,761 B2 | 10/2003 | Shin et al. |
| 6,971,383 B2 | 12/2005 | Hickey et al. |
| 7,377,277 B2 | 5/2008 | Hickey et al. |
| 8,061,362 B2 | 11/2011 | Mua et al. |
| 8,714,161 B2 | 5/2014 | Liu |
| 8,857,446 B2 | 10/2014 | Wu |
| 8,881,737 B2 | 11/2014 | Collett et al. |
| 9,439,456 B2 | 9/2016 | Liu |
| 9,848,644 B2 | 12/2017 | Plunkett et al. |
| 9,930,915 B2 | 4/2018 | Worm et al. |
| 10,375,994 B2 | 8/2019 | Mironov et al. |
| 10,609,958 B2 | 4/2020 | Robinson et al. |
| 10,856,575 B2 | 12/2020 | Gill et al. |
| 2002/0005207 A1 | 1/2002 | Wrenn et al. |
| 2002/0078951 A1 | 6/2002 | Nichols et al. |
| 2003/0209531 A1 | 11/2003 | Mattis |
| 2003/0226837 A1 | 12/2003 | Blake et al. |
| 2004/0089314 A1 | 5/2004 | Felter et al. |
| 2004/0129280 A1 | 7/2004 | Woodson et al. |
| 2004/0149296 A1 | 8/2004 | Rostami et al. |
| 2004/0200488 A1 | 10/2004 | Felter et al. |
| 2005/0211698 A1 | 9/2005 | Kirkman |
| 2006/0070633 A1 | 4/2006 | Rostami et al. |
| 2006/0191893 A1 | 8/2006 | Weinfield et al. |
| 2009/0272379 A1 | 11/2009 | Thorens et al. |
| 2011/0048434 A1 | 3/2011 | Chen et al. |
| 2011/0192408 A1 | 8/2011 | Inagaki et al. |
| 2011/0204038 A1 | 8/2011 | Feng et al. |
| 2011/0271971 A1 | 11/2011 | Conner et al. |
| 2012/0111347 A1 | 5/2012 | Hon |
| 2012/0222690 A1 | 9/2012 | Branton et al. |
| 2012/0234821 A1 | 9/2012 | Shimizu |
| 2012/0260927 A1 | 10/2012 | Liu |
| 2012/0285475 A1 | 11/2012 | Liu |
| 2013/0037041 A1 | 2/2013 | Worm et al. |
| 2013/0056013 A1 | 3/2013 | Terry et al. |
| 2013/0081642 A1 | 4/2013 | Safari |
| 2013/0152953 A1 | 6/2013 | Mua et al. |
| 2013/0167853 A1 | 7/2013 | Liu |
| 2013/0180516 A1 | 7/2013 | Damani et al. |
| 2013/0192617 A1 | 8/2013 | Thompson |
| 2013/0192618 A1 | 8/2013 | Li et al. |
| 2013/0213419 A1 | 8/2013 | Tucker et al. |
| 2013/0255702 A1 | 10/2013 | Griffith, Jr. et al. |
| 2013/0319436 A1 | 12/2013 | Liu |
| 2013/0319438 A1 | 12/2013 | Liu |
| 2013/0340778 A1 | 12/2013 | Liu |
| 2014/0000638 A1 | 1/2014 | Sebastian et al. |
| 2014/0007891 A1 | 1/2014 | Liu |
| 2014/0014126 A1 | 1/2014 | Peleg et al. |
| 2014/0048086 A1 | 2/2014 | Zhanghua |
| 2014/0060554 A1 | 3/2014 | Collett et al. |
| 2014/0076337 A1 | 3/2014 | Woodman et al. |
| 2014/0103020 A1 | 4/2014 | Al-Qaffas |
| 2014/0123989 A1 | 5/2014 | LaMothe |
| 2014/0130816 A1 | 5/2014 | Liu |
| 2014/0150810 A1 | 6/2014 | Hon |
| 2014/0196733 A1 | 7/2014 | Liu |
| 2014/0196734 A1 | 7/2014 | Liu |
| 2014/0202476 A1* | 7/2014 | Egoyants ............... A24F 40/46 131/329 |
| 2014/0209112 A1 | 7/2014 | Awty et al. |
| 2014/0216484 A1 | 8/2014 | Liu |
| 2014/0224244 A1 | 8/2014 | Liu |
| 2014/0230835 A1 | 8/2014 | Saliman |
| 2014/0238421 A1 | 8/2014 | Shapiro |
| 2014/0238422 A1 | 8/2014 | Plunkett et al. |
| 2014/0253144 A1 | 9/2014 | Novak, III et al. |
| 2014/0261486 A1 | 9/2014 | Potter et al. |
| 2014/0261487 A1 | 9/2014 | Chapman et al. |
| 2014/0261490 A1 | 9/2014 | Kane |
| 2014/0261500 A1 | 9/2014 | Park |
| 2014/0262856 A1 | 9/2014 | Damiani et al. |
| 2014/0270729 A1 | 9/2014 | Depiano et al. |
| 2014/0271951 A1 | 9/2014 | Mua et al. |
| 2014/0283857 A1 | 9/2014 | Liu |
| 2014/0290674 A1 | 10/2014 | Liu |
| 2014/0299137 A1 | 10/2014 | Kieckbusch et al. |
| 2014/0305454 A1 | 10/2014 | Rinker et al. |
| 2014/0311505 A1 | 10/2014 | Liu |
| 2014/0338680 A1 | 11/2014 | Abramov et al. |
| 2014/0355969 A1 | 12/2014 | Stern |
| 2014/0360515 A1 | 12/2014 | Vasiliev et al. |
| 2014/0366898 A1 | 12/2014 | Monsees et al. |
| 2015/0000684 A1 | 1/2015 | Wu |
| 2015/0020830 A1 | 1/2015 | Koller |
| 2015/0020831 A1 | 1/2015 | Weigensberg et al. |
| 2015/0027461 A1 | 1/2015 | Liu |
| 2015/0027473 A1 | 1/2015 | Graf |
| 2015/0034104 A1 | 2/2015 | Zhou |
| 2015/0040922 A1 | 2/2015 | Dube et al. |
| 2015/0053215 A1 | 2/2015 | Liu |
| 2015/0053218 A1 | 2/2015 | Liu |
| 2015/0083147 A1 | 3/2015 | Schiff et al. |
| 2015/0090256 A1 | 4/2015 | Chung |
| 2015/0101625 A1 | 4/2015 | Newton et al. |
| 2015/0101626 A1 | 4/2015 | Li et al. |
| 2015/0157055 A1 | 6/2015 | Lord |
| 2015/0173422 A1 | 6/2015 | Liu |
| 2015/0181936 A1 | 7/2015 | Lyubomirskiy et al. |
| 2015/0181938 A1 | 7/2015 | Metrangolo et al. |
| 2015/0196055 A1 | 7/2015 | Liu |
| 2015/0196059 A1 | 7/2015 | LIu |
| 2015/0201674 A1 | 7/2015 | Dooly et al. |
| 2015/0216232 A1 | 8/2015 | Bless et al. |
| 2015/0223523 A1 | 8/2015 | McCullough |
| 2015/0245654 A1 | 9/2015 | Memari et al. |
| 2015/0245658 A1 | 9/2015 | Worm et al. |
| 2015/0245669 A1 | 9/2015 | Cadieux et al. |
| 2015/0257445 A1 | 9/2015 | Henry, Jr. et al. |
| 2015/0272217 A1 | 10/2015 | Chen |
| 2015/0272218 A1 | 10/2015 | Chen |
| 2015/0282527 A1 | 10/2015 | Henry, Jr. |
| 2015/0305408 A1 | 10/2015 | Liu |
| 2015/0313282 A1 | 11/2015 | Ademe et al. |
| 2015/0313283 A1 | 11/2015 | Collett et al. |
| 2015/0313284 A1 | 11/2015 | Liu |
| 2015/0316270 A1 | 11/2015 | Koos et al. |
| 2015/0366265 A1 | 12/2015 | Lansing |

(56) References Cited

U.S. PATENT DOCUMENTS

| | | |
|---|---|---|
| 2016/0007651 A1 | 1/2016 | Ampolini et al. |
| 2016/0029698 A1 | 2/2016 | Xiang |
| 2016/0066621 A1 | 3/2016 | Depiano et al. |
| 2016/0073694 A1 | 3/2016 | Liu |
| 2016/0089508 A1 | 3/2016 | Smith et al. |
| 2016/0095352 A1 | 4/2016 | Liu |
| 2016/0095357 A1 | 4/2016 | Burton |
| 2016/0113326 A1 | 4/2016 | Li et al. |
| 2016/0128386 A1 | 5/2016 | Chen |
| 2016/0128389 A1 | 5/2016 | Lamb et al. |
| 2016/0135505 A1 | 5/2016 | Li et al. |
| 2016/0138795 A1 | 5/2016 | Meinhart et al. |
| 2016/0161108 A1 | 6/2016 | Chua et al. |
| 2016/0183598 A1 | 6/2016 | Tucker et al. |
| 2016/0262455 A1 | 9/2016 | Chen |
| 2017/0042230 A1 | 2/2017 | Cameron |
| 2017/0108210 A1 | 4/2017 | Meinhart et al. |
| 2017/0318862 A1 | 11/2017 | Mironov et al. |
| 2017/0347711 A1 | 12/2017 | Litten et al. |
| 2017/0347712 A1 | 12/2017 | Singh |
| 2017/0347713 A1 | 12/2017 | Robinson et al. |
| 2018/0015385 A1 | 1/2018 | Meinhart |
| 2018/0042302 A1 | 2/2018 | Robinson et al. |
| 2018/0070635 A1 | 3/2018 | Litten |
| 2018/0168233 A1 | 6/2018 | Depiano et al. |
| 2018/0271153 A1 | 9/2018 | John et al. |
| 2019/0082734 A1 | 3/2019 | Alarcon |
| 2020/0000148 A1 | 1/2020 | Horrod et al. |
| 2020/0029618 A1 | 1/2020 | Fraser et al. |

FOREIGN PATENT DOCUMENTS

| | | |
|---|---|---|
| CA | 2047823 A1 | 2/1992 |
| CA | 2967177 A1 | 5/2016 |
| CA | 3050171 A1 | 7/2018 |
| CN | 1102964 A | 5/1995 |
| CN | 1126426 A | 7/1996 |
| CN | 101518361 A | 9/2009 |
| CN | 103876288 A | 6/2014 |
| CN | 204888733 U | 12/2015 |
| EP | 0438862 | 7/1991 |
| EP | 0640297 A1 | 3/1995 |
| EP | 2316286 | 5/2011 |
| EP | 3571895 A1 | 11/2019 |
| JP | H07147965 A | 6/1995 |
| JP | 2003526480 A | 9/2003 |
| JP | 2005516647 A | 6/2005 |
| JP | 2010131366 A | 6/2010 |
| JP | 2013532994 A | 8/2013 |
| JP | 2014076065 A | 5/2014 |
| KR | 20020086624 A | 11/2002 |
| RU | 2097996 C1 | 12/1997 |
| WO | 00/28842 | 5/2000 |
| WO | 01/68169 A1 | 9/2001 |
| WO | 03049792 A1 | 6/2003 |
| WO | 2013022936 A1 | 2/2013 |
| WO | 2013034460 A1 | 3/2013 |
| WO | 2013/152873 | 10/2013 |
| WO | 2013159245 A1 | 10/2013 |
| WO | 2013160112 A2 | 10/2013 |
| WO | 2014004648 A1 | 1/2014 |
| WO | 2014012905 A1 | 1/2014 |
| WO | 2014012906 A1 | 1/2014 |
| WO | 2014032276 A1 | 3/2014 |
| WO | 2014037794 A2 | 3/2014 |
| WO | 2014150979 A2 | 9/2014 |
| WO | 2014177693 A1 | 11/2014 |
| WO | 2014177696 A1 | 11/2014 |
| WO | 2014201432 A1 | 12/2014 |
| WO | 2015/082648 | 6/2015 |
| WO | 2015/082653 | 6/2015 |
| WO | 2015116934 A1 | 8/2015 |
| WO | 2015177254 A1 | 11/2015 |
| WO | 2015177264 A1 | 11/2015 |
| WO | 2016-120344 | 8/2016 |

OTHER PUBLICATIONS

Office Action for Malaysian Application No. PI2019003782, dated Aug. 8, 2022, 3 pages.
Decision of Refusal mailed May 11, 2021 for Japanese Application No. 2019-043555, 6 pages.
Examination Report mailed Jun. 29, 2018 for Australian Application No. 201612042, 6 pages.
Examination Report No. 1 for Australian Patent Application No. 2020217428, dated Aug. 3, 2021, 8 pages.
Extended European Search Report for Application No. 20190829.0, mailed on Mar. 1, 2021, 8 pages.
First Office Action for Chinese Application No. 201880006689.5, mailed on Feb. 3, 2021, 22 pages.
International Preliminary Report on Patentability for Application No. PCT/EP2018/050907, mailed on Aug. 1, 2019, 9 pages.
International Preliminary Report on Patentability for Application No. PCT/EP2016/051727, mailed on Aug. 10, 2017, 9 pages.
International Search Report and Written Opinion for Application No. PCT/EP2016/051727, mailed on Jul. 25, 2016, 12 pages.
Khan Academy, "Whal is thermal conductivity?," Retrieved from https://www.khanacademy.org/science/physics/hermodynamics/specific-heat-and-heat-transfer/a/what-is-lhermal-conductivity, Oct. 6, 2017, 13 pages.
Krishnakumar R.T.R.K., et al., "Determination of Effective Thermal Conductivity of Perforated Plates with Low Porosities Used as Matrix Heat Exchanger Core Surfaces," International Journal of Scientific and Engineering Research, vol. 5, No. 7, Jul. 2014, pp. 790-794.
Notice of acceptance mailed May 11, 2020 for Australian Application No. 2019200069, 3 pages.
Office Action dated Jun. 1, 2021 for Canadian Application No. 3,050,171, 4 pages.
Office Action for Chinese Application No. 201680019503.0, mailed on Aug. 19, 2021, 17 pages.
Office Action for Japanese Application No. 2019-043555, mailed Nov. 30, 2021, 5 pages.
Office Action for Korean Application No. 10-2020-7021464, mailed Dec. 28, 2021, 11 pages.
Office Action for Russian Application No. 201708626 mailed on Jul. 23, 2020, 7 pages.
Office Action mailed Jul. 5, 2019 for Chinese Application No. 201680019503.0, 24 pages.
Office Action mailed Aug. 14, 2018 for Japanese Application No. 2017-539638, 9 pages.
Office Action mailed Sep. 15, 2020 for Japanese Application No. 2019043555, 6 pages.
Office Action mailed May 22, 2020 for Korean Application No. 10-2019-7011902, 6 pages.
Office Action mailed May 25, 2021 for Korean Application No. 10-2019-7020693, 6 pages.
Office Action mailed Feb. 26, 2019 for Canadian Application No. 2973305, 6 pages.
Office Action mailed Apr. 28, 2020 for Japanese Application No. 2019043555, 5 pages.
Office Action mailed Aug. 30, 2018 for Korean Application No. 10-2017-7023910, 21 pages.
Office Action mailed Nov. 6, 2020 for Ukrainian Application No. 201900424, 4 pages.
Office Action mailed May 9, 2019 for Korean Application No. 10-2019-7011902, 4 pages.
Third Office Action for Chinese Application No. 201880006689.5, mailed on Dec. 31, 2021, 16 pages.

* cited by examiner

APPARATUS FOR HEATING SMOKABLE MATERIAL

PRIORITY CLAIM

The present application is a Continuation of U.S. application Ser. No. 17/858,888, filed Jul. 6, 2022, which in turn is a Continuation of U.S. application Ser. No. 16/478,724, filed Jul. 17, 2019, now U.S. Pat. No. 11,503,676, issued Nov. 15, 2022, which in turn is a US National Phase entry of PCT Application No. PCT/EP2018/050907, filed Jan. 15, 2018, which claims priority from Great Britain Patent Application No. 1700812.9, filed Jan. 17, 2017, each of which is hereby fully incorporated herein by reference.

TECHNICAL FIELD

The present invention relates to articles for use with apparatus for heating smokable material to volatilise at least one component of the smokable material, to apparatus for heating smokable material to volatilise at least one component of the smokable material, and to systems comprising such articles and such apparatus.

BACKGROUND

Smoking articles such as cigarettes, cigars and the like burn tobacco during use to create tobacco smoke. Attempts have been made to provide alternatives to these articles by creating products that release compounds without combusting. Examples of such products are so-called "heat not burn" products or tobacco heating devices or products, which release compounds by heating, but not burning, material. The material may be, for example, tobacco or other non-tobacco products, which may or may not contain nicotine.

SUMMARY

A first aspect of the present invention provides an article for use with apparatus for heating smokable material to volatilise at least one component of the smokable material, the article comprising: a carrier having plural thermally-conductive portions on which are locatable respective discrete quantities of smokable material; wherein, between the portions of the carrier, the carrier is shaped to form a thermal barrier for inhibiting heat conduction from one or more of the portions of the carrier towards another of the portions of the carrier in use.

In an exemplary embodiment, between the portions of the carrier and as compared to the portions of the carrier, the carrier is shaped to form the thermal barrier.

In an exemplary embodiment, the article comprises the respective discrete quantities of smokable material on the plural thermally-conductive portions of the carrier.

In an exemplary embodiment, the smokable material is in the form of a gel or thin film.

In an exemplary embodiment, the carrier is shaped to form thermal barriers between respective pairs of the portions of the carrier.

In an exemplary embodiment, the, or each, thermal barrier surrounds a respective one of the portions of the carrier.

In an exemplary embodiment, the, or each, thermal barrier comprises one or more holes through the carrier.

In an exemplary embodiment, the, or each, thermal barrier comprises one or more channels or blind holes in the carrier.

In an exemplary embodiment, the article comprises a mass of thermally-insulating material in the channel(s) or blind hole(s) of the, or each, thermal barrier.

In an exemplary embodiment, the thermally-insulating material comprises a polymer.

In an exemplary embodiment, the thermally-insulating material has a thermal conductivity of no more than 0.5 W/(m·K).

In an exemplary embodiment, the portions of the carrier are arranged as a two-dimensional array.

In an exemplary embodiment, each of the portions of the carrier is made from heating material that is heatable by penetration with a varying magnetic field.

In an exemplary embodiment, the heating material comprises one or more materials selected from the group consisting of: an electrically-conductive material, a magnetic material, and a magnetic electrically-conductive material.

In an exemplary embodiment, the heating material comprises a metal or a metal alloy.

In an exemplary embodiment, the heating material comprises one or more materials selected from the group consisting of: aluminium, gold, iron, nickel, cobalt, conductive carbon, graphite, plain-carbon steel, stainless steel, ferritic stainless steel, steel, copper, and bronze.

A second aspect of the present invention provides an article for use with apparatus for heating smokable material to volatilise at least one component of the smokable material, the article comprising or consisting of: a carrier having a surface; and smokable material, in the form of a gel or thin film, on the surface of the carrier.

In an exemplary embodiment, the smokable material is coextensive or substantially coextensive with the surface of the carrier.

In an exemplary embodiment, the smokable material comprises plural discrete quantities of the smokable material on the surface of the carrier.

In an exemplary embodiment, the carrier is a sheet.

In an exemplary embodiment, the carrier has, or comprises a material having, a thermal conductivity of at least 10 W/(m·K) or at least 90 W/(m·K) or at least 200 W/(m·K).

In an exemplary embodiment, the carrier comprises nickel and/or aluminium.

In an exemplary embodiment, the carrier comprises a laminate, and wherein the laminate comprises a layer of nickel and a layer of aluminium.

In an exemplary embodiment, the layer of aluminium is located between the layer of nickel and the smokable material. In another exemplary embodiment, the layer of nickel is located between the layer of aluminium and the smokable material.

In an exemplary embodiment, the carrier comprises a laminate, and wherein the laminate comprises a layer of nickel and a layer of paper.

In an exemplary embodiment, the layer of paper is located between the layer of nickel and the smokable material. In another exemplary embodiment, the layer of nickel is located between the layer of paper and the smokable material.

A third aspect of the present invention provides apparatus for heating smokable material to volatilise at least one component of the smokable material, the apparatus comprising: the article of the first aspect of the present invention or the article of the second aspect of the present invention; and a heating device for heating the thermally-conductive portions of the carrier.

A fourth aspect of the present invention provides apparatus for heating smokable material to volatilise at least one component of the smokable material, the apparatus comprising: a heating zone for receiving an article comprising smokable material; a substrate comprising plural thermally-conductive portions, wherein, between the portions of the substrate, the substrate is shaped to create a thermal barrier for inhibiting heat conduction from one or more of the portions of the substrate towards another of the portions of the substrate in use; and a heating device for heating the thermally-conductive portions of the substrate to thereby heat portions of the heating zone.

In an exemplary embodiment, between the portions of the substrate and as compared to the portions of the substrate, the substrate is shaped to form the thermal barrier.

In an exemplary embodiment, the substrate is shaped to form thermal barriers between respective pairs of the portions of the substrate.

In an exemplary embodiment, the, or each, thermal barrier surrounds a respective one of the portions of the substrate.

In an exemplary embodiment, the substrate comprises heating material that is heatable by penetration with a varying magnetic field, and a nickel coating on the heating material.

In an exemplary embodiment, the heating material comprises one or more materials selected from the group consisting of: an electrically-conductive material, a magnetic material, and a magnetic electrically-conductive material.

In an exemplary embodiment, the heating material comprises a metal or a metal alloy.

In an exemplary embodiment, the heating material comprises one or more materials selected from the group consisting of: aluminium, gold, iron, nickel, cobalt, conductive carbon, graphite, plain-carbon steel, stainless steel, ferritic stainless steel, steel, copper, and bronze.

In an exemplary embodiment, the heating device comprises plural heaters for heating respective ones of the thermally-conductive portions.

In an exemplary embodiment, each of the thermally-conductive portions is made from heating material that is heatable by penetration with a varying magnetic field; and wherein the plural heaters comprise respective magnetic field generators for generating varying magnetic fields for penetrating the respective thermally-conductive portions in use.

In an exemplary embodiment, the apparatus comprises a printed circuit board, wherein the magnetic field generators comprise respective coils formed in or on the printed circuit board.

In an exemplary embodiment, the apparatus comprises a controller for controlling operation of at least one of the plural heaters independently of at least one other of the plural heaters.

A fifth aspect of the present invention provides a system for heating smokable material to volatilise at least one component of the smokable material, the system comprising: the article of the first aspect of the present invention or the article of the second aspect of the present invention; and apparatus comprising a heating zone for receiving the article, and a heating device for heating the thermally-conductive portions of the carrier of the article when the article is located in the heating zone.

In an exemplary embodiment, the heating device comprises plural heaters for heating respective ones of the thermally-conductive portions.

In an exemplary embodiment, each of the thermally-conductive portions is made from heating material that is heatable by penetration with a varying magnetic field; and wherein the plural heaters comprise respective magnetic field generators for generating varying magnetic fields for penetrating the respective thermally-conductive portions in use.

In an exemplary embodiment, the apparatus comprises a printed circuit board, wherein the magnetic field generators comprise respective coils formed in or on the printed circuit board.

In an exemplary embodiment, the apparatus comprises a controller for controlling operation of at least one of the plural heaters independently of at least one other of the plural heaters.

In an exemplary embodiment, the article is the article of the first aspect of the present invention, the apparatus is the apparatus of the fourth aspect of the present invention, and the thermally-conductive portions of the carrier of the article align with the thermally-conductive portions of the substrate of the apparatus when the article is in the heating zone.

BRIEF DESCRIPTION OF THE DRAWINGS

Embodiments of the invention will now be described, by way of example only, with reference to the accompanying drawings, in which.

DETAILED DESCRIPTION

Figure 1:
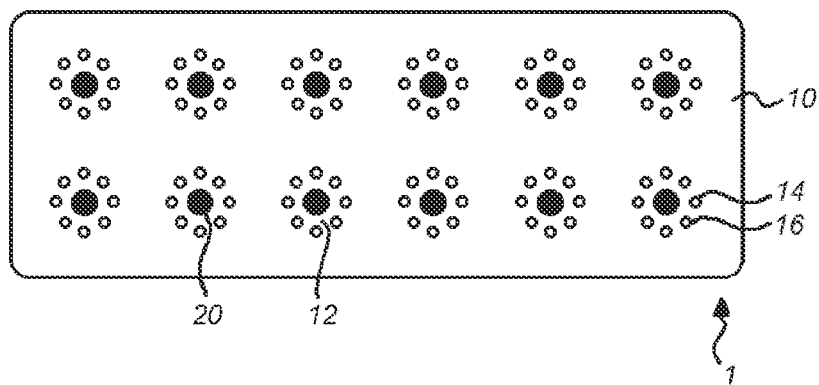
FIG. 1 shows a schematic plan view of an example of an article for use with apparatus for heating smokable material to volatilise at least one component of the smokable material.

As used herein, the term "smokable material" includes materials that provide volatilised components upon heating, typically in the form of vapour or an aerosol. "Smokable material" may be a non-tobacco-containing material or a tobacco-containing material. "Smokable material" may for example, include one or more of tobacco per se, tobacco derivatives, expanded tobacco, reconstituted tobacco, tobacco extract, homogenised tobacco or tobacco substitutes. The smokable material can be in the form of ground tobacco, cut rag tobacco, extruded tobacco, reconstituted tobacco, reconstituted smokable material, liquid, gel, gelled sheet, powder, or agglomerates, or the like. "Smokable material" also may include other, non-tobacco, products, which, depending on the product, may or may not contain nicotine. "Smokable material" may comprise one or more humectants, such as glycerol or propylene glycol.

As used herein, the term "heating material" or "heater material" refers to material that is heatable by penetration with a varying magnetic field.

Induction heating is a process in which an electrically-conductive object is heated by penetrating the object with a varying magnetic field. The process is described by Faraday's law of induction and Ohm's law. An induction heater may comprise an electromagnet and a device for passing a varying electrical current, such as an alternating current, through the electromagnet. When the electromagnet and the object to be heated are suitably relatively positioned so that the resultant varying magnetic field produced by the electromagnet penetrates the object, one or more eddy currents are generated inside the object. The object has a resistance to the flow of electrical currents. Therefore, when such eddy currents are generated in the object, their flow against the electrical resistance of the object causes the object to be heated. This process is called Joule, ohmic, or resistive heating. An object that is capable of being inductively heated is known as a susceptor.

It has been found that, when the susceptor is in the form of a closed circuit, magnetic coupling between the susceptor and the electromagnet in use is enhanced, which results in greater or improved Joule heating.

Magnetic hysteresis heating is a process in which an object made of a magnetic material is heated by penetrating the object with a varying magnetic field. A magnetic material can be considered to comprise many atomic-scale magnets, or magnetic dipoles. When a magnetic field penetrates such material, the magnetic dipoles align with the magnetic field. Therefore, when a varying magnetic field, such as an alternating magnetic field, for example as produced by an electromagnet, penetrates the magnetic material, the orientation of the magnetic dipoles changes with the varying applied magnetic field. Such magnetic dipole reorientation causes heat to be generated in the magnetic material.

When an object is both electrically-conductive and magnetic, penetrating the object with a varying magnetic field can cause both Joule heating and magnetic hysteresis heating in the object. Moreover, the use of magnetic material can strengthen the magnetic field, which can intensify the Joule heating.

In each of the above processes, as heat is generated inside the object itself, rather than by an external heat source by heat conduction, a rapid temperature rise in the object and more uniform heat distribution can be achieved, particularly through selection of suitable object material and geometry, and suitable varying magnetic field magnitude and orientation relative to the object. Moreover, as induction heating and magnetic hysteresis heating do not require a physical connection to be provided between the source of the varying magnetic field and the object, design freedom and control over the heating profile may be greater, and cost may be lower.

Figure 2:
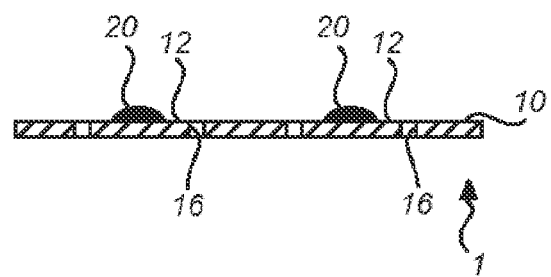
FIG. 2 shows a schematic cross-sectional view of the article of FIG. 1.

Referring to FIGS. 1 and 2, there are shown schematic plan and cross-sectional views of an example of an article according to an embodiment of the invention. The article 1 is for use with apparatus for heating smokable material to volatilise at least one component of the smokable material, such as the apparatus 100 shown in FIG. 13 and described below.

The article 1 comprises a carrier 10 having a surface and plural discrete quantities of smokable material 20 on the surface of the carrier 10. In this embodiment, the surface is a major surface of the carrier 10. The carrier 10 of this embodiment is a sheet of mild steel with a thickness of about 25 μm. However, in other embodiments the sheet may be made of a different material and/or could have a different thickness, such as a thickness of between 10 μm and 50 μm. The steel has a thermal conductivity of over 10 W/(m·K). In some embodiments, the mild steel may be coated or electroplated with nickel. In such cases, the nickel may for example have a thickness of less than 5 μm, such as between 2 μm and 3 μm. Providing the carrier 10 with only a relatively small thickness may help to reduce the time required to heat the carrier 10 in use.

The carrier 10 has plural thermally-conductive portions 12 on which the respective discrete quantities of smokable material 20 are located. The discrete quantities of smokable material 20 are in thermal contact with the respective thermally-conductive portions 12. Indeed, in this embodiment, the discrete quantities of smokable material 20 are in surface contact with the respective thermally-conductive portions 12.

Any specific one of the discrete quantities of smokable material 20 is heatable in use by heating the thermally-conductive portion 12 of the carrier 10 on which the specific quantity of smokable material 20 is located. Such heating may be achieved in one of many ways. For example, the appropriate thermally-conductive portion 12 may be heated by applying heat energy to the thermally-conductive portion 12, such as by thermal radiation or thermal conduction. Alternatively, when the thermally-conductive portion 12 of the carrier 10 is made from heating material that is heatable by penetration with a varying (e.g. alternating) magnetic field, as is the case in this embodiment, the thermally-conductive portion 12 may be heated inductively by penetrating the thermally-conductive portion 12 with the varying (e.g. alternating) magnetic field. This principle of heating will be described in more detail below with reference to the apparatus 100 of FIG. 13, which has plural magnetic field generators for generating varying magnetic fields for penetrating the respective thermally-conductive portions 12 of the carrier 10 in use.

The article 1 is configured so that one of the discrete quantities of smokable material 20 is heatable in use while inhibiting heating of another of the discrete quantities of smokable material 20. More specifically, between the portions 12 of the carrier 10, the carrier 10 is shaped to form thermal barriers 14 for inhibiting heat conduction from one of the portions 12 of the carrier 10 towards another of the portions 12 of the carrier 10 in use. That is, the geometry of the carrier 10 is such as to at least partially thermally insulate the thermally-conductive portions 12 of the carrier 10 from each other, to help prevent or reduce heat conduction from one of the portions 12 towards another of the portions 12 in use. In this embodiment, the carrier 10 is shaped to form the thermal barriers 14 between the portions 12 of the carrier 10 and as compared to the portions 12 of the carrier 10.

In this embodiment, the carrier 10 comprises twelve thermally-conductive portions 12, and the carrier 10 is shaped to form thermal barriers 14 between respective pairs of the portions 12 of the carrier 10. More specifically, the carrier 10 is shaped to form plural thermal barriers 14 that surround respective ones of the thermally-conductive portions 12 of the carrier 10. Therefore, any specific one or plurality of the portions 12 is heatable in use without, or without significant, heating of any of the other portions 12 of the carrier 10. Therefore, each, or a subset, of the discrete quantities of smokable material 20 on the portions 12 of the carrier 10 is selectively heatable to volatilise at least one component of the smokable material 20, without heating any other of the discrete quantities of smokable material 20 to a degree that would similarly result in such volatilisation.

In this embodiment, the twelve thermally-conductive portions 12 of the carrier 10 are arranged in two rows of six. The thermally-conductive portions 12 are therefore arranged as a two-dimensional array. In other embodiments, the carrier 10 may comprise more or fewer thermally-conductive portions 12, and in some embodiments, the portions 12 may be arranged as a one-dimensional array, for example. That is, all of the thermally-conductive portions 12 of the carrier 10 may be relatively aligned in a single row, which may be a straight or linear row.

In this embodiment, each of the thermal barriers 14 comprises a plurality of spaced-apart through holes or perforations 16 through the carrier 10. The effect of the through holes or perforations 16 is to reduce the cross-sectional area of the carrier 10 at the thermal barrier 14, which impairs heat conduction across the thermal barrier 14. The presence of air in the through holes or perforations 16 may also contribute to the thermal insulation properties. The perforations 16 of each thermal barrier 14 are arranged on a circular path that surrounds one of the thermally-conductive portions 12 of the carrier 10. However, in other embodiments, the path may be other than circular, such as polygonal or elliptical. In this embodiment, each of the perforations 16 is itself circular. However, in other embodiments, one or more of the perforations 16 of a thermal barrier 14 may be other than circular, such as polygonal, elliptical or elongate or slot-shaped.

In this embodiment, each thermal barrier 14 comprises eight through holes or perforations 16 through the carrier 10. That is, there is a total of eight holes on the path. However, in other embodiments, one or each of the thermal barriers 14 may comprise more through holes or perforations 16 through the carrier 10, such as between twenty and thirty holes. In some embodiments, one or each of the thermal barriers 14 may comprise fewer holes 16 through the carrier 10. For example, in some embodiments, the thermal barrier 14 may comprise or consist of only one or two holes 16 through the carrier 10. In such embodiment, the through hole(s) 16 may be elongate or slot-shaped in the plane of the carrier, so as to sufficiently resist the conduction of heat across the thermal barrier 14.

The perforations 16 may be formed by laser etching the carrier 10, by punching the carrier 10, or by any other suitable method.

In some variations to this embodiment, the, or each, thermal barrier 14 of the carrier 10 may comprise one or more channels or blind holes in the carrier 10. The one or more channels or blind holes may be provided in addition to, or instead of, the through hole(s) or perforations 16 discussed above.

Figure 3:
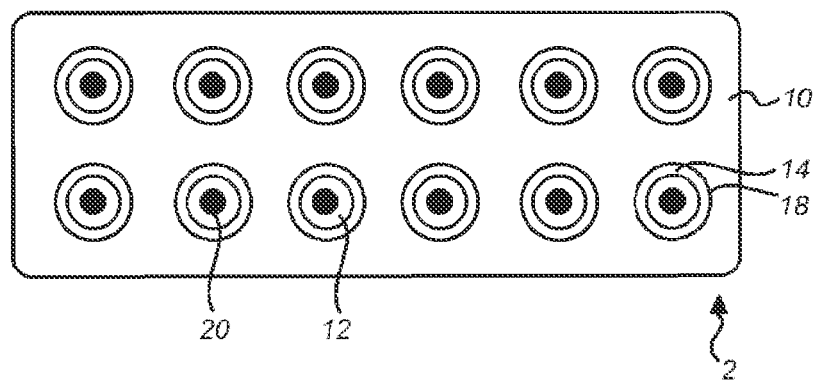
FIG. 3 shows a schematic plan view of an example of another article for use with apparatus for heating smokable material to volatilise at least one component of the smokable material.
Figure 4:
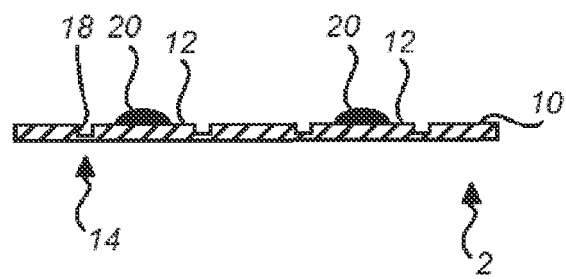
FIG. 4 shows a schematic cross-sectional view of the article of FIG. 3.

For example, referring to FIGS. 3 and 4, there are shown schematic plan and cross-sectional views of an example of an article according to another embodiment of the invention. The article 2 is for use with apparatus for heating smokable material to volatilise at least one component of the smokable material, such as the apparatus 100 shown in FIG. 13 and described below.

In this embodiment, the article 2 is identical to the article 1 of FIGS. 1 and 2, except for the form of the thermal barriers 14. In this embodiment, each of the thermal barriers 14 comprises a channel 18 in the carrier 10. That is, the channel 18 is formed as a depression in a surface or side of the carrier 10, with which surface or side the discrete quantities of smokable material 20 are in surface contact. The effect of the channel 18 is to thin the carrier 10 at the barrier 14, so as to reduce the cross-sectional area of the carrier 10 at the thermal barrier 14 to therefore impair heat conduction across the thermal barrier 14. The channel 18 of each thermal barrier 14 is circular and surrounds one of the thermally-conductive portions 12 of the carrier 10. However, in other embodiments, the channel 18 of the, or each, thermal barrier 14 of the carrier 10 may be other than circular, such as polygonal or elliptical. In some embodiments, the channels 18 or blind holes may not surround the respective thermally-conductive portions 12 of the carrier 10. In some such embodiments, the channels 18 or blind holes may be linear or non-linear, such as arcuate.

In this embodiment, each thermal barrier 14 comprises one channel 18 in the carrier 10. However, in other embodiments, a thermal barrier 14 may comprise more than one channel or blind hole in the carrier 10, such as between two and thirty channels or blind holes. In some embodiments, the channels or blind holes may be elongate or slot-shaped to help resist the conduction of heat across the thermal barrier 14.

In this embodiment, the channels 18 of the thermal barriers 14 may be formed by pressing, etching or embossing the carrier 10, for example. It will be noted from FIG. 4 that the side of the carrier 10 opposite that on which the discrete quantities of smokable material 20 are located is substantially flat. In other embodiments, that may not be true, and that may be due to the form of channel(s) or blind hole(s) of the thermal barriers 14.

Figure 5:
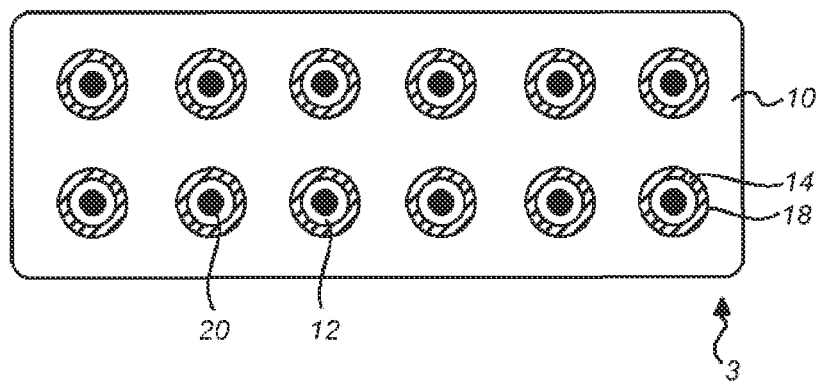
FIG. 5 shows a schematic plan view of an example of another article for use with apparatus for heating smokable material to volatilise at least one component of the smokable material.
Figure 6:
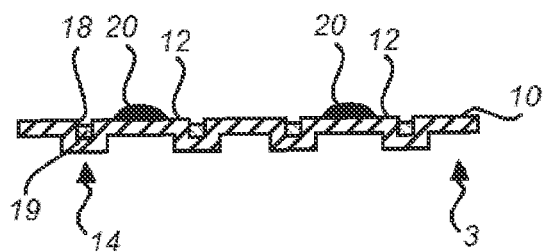
FIG. 6 shows a schematic cross-sectional view of the article of FIG. 5.

For example, referring to FIGS. 5 and 6, there are shown schematic plan and cross-sectional views of an example of an article according to another embodiment of the invention. The article 3 is for use with apparatus for heating smokable material to volatilise at least one component of the smokable material, such as the apparatus 100 shown in FIG. 13 and described below.

In this embodiment, the article 3 is identical to the article 2 of FIGS. 3 and 4, except for the form of the thermal barriers 14. In this embodiment, each of the thermal barriers 14 comprises a channel 18 that is embossed in the carrier 10 to the extent that a floor of the channel 18 protrudes from the side of the carrier 10 opposite that on which the discrete quantities of smokable material 20 are located. The effect of each of the channels 18 is to lengthen the carrier 10 along a route that extends from one of the thermally-conductive portions 12 to another of the thermally-conductive portions 12 via the floor of the channel 18. This increases the surface area of the carrier at the thermal barrier 14, to help dissipate heat from the carrier 10 at the thermal barrier 14 and thus impair heat conduction across the thermal barrier 14.

The channel 18 of each thermal barrier 14 is circular and surrounds one of the thermally-conductive portions 12 of the carrier 10. However, in other embodiments, the channel or blind hole of the, or each, thermal barrier 14 of the carrier 10 may be other than circular, such as polygonal or elliptical. In some embodiments, the channels or blind holes may not surround the respective thermally-conductive portions 12 of the carrier 10. In some such embodiments, the channels 18 or blind holes may be linear or non-linear, such as arcuate.

In this embodiment, each thermal barrier 14 comprises one channel 18 in the carrier 10. However, in other embodiments, a thermal barrier 14 may comprise more than one channel 18 or blind hole in the carrier 10, such as between two and thirty channels or blind holes. In some embodiments, the channels or blind holes may be elongate or slot-shaped to increase the surface area of the carrier 10 adequately to help resist the conduction of heat across the thermal barrier 14.

In this embodiment, a mass of thermally-insulating material 19 is located in the channel 18 of each of the thermal barriers 14. At each thermal barrier 14, the thermally-insulating material 19 helps to further reduce the transfer of heat energy from the thermally-conductive portion 12 on one side of the thermal barrier 14 towards the other side of the thermal barrier 14. Preferably, the thermally-insulating material 19 has a lower thermal conductivity than air. The thermally-insulating material 19 may be a polymer or plastics material such as polyether ether ketone (PEEK), or a cellulosic material such as wood or paper, or reconstituted tobacco. Preferably, the thermally-insulating material has a thermal conductivity of no more than 0.5 W/(m·K).

As variations to the embodiments discussed above with reference to FIGS. 3 and 4, a mass of thermally-insulating material may be located in the channels or blind holes of the thermal barriers 14 of the article 2 or its disclosed variants. Such a mass of thermally-insulating material may comprise any of the materials discussed in the preceding paragraph.

Figure 7:
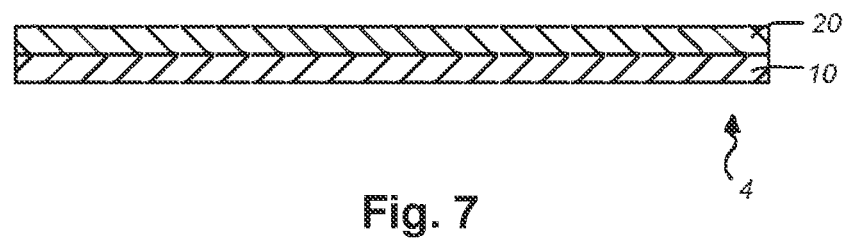
FIG. 7 shows a schematic cross-sectional view of an example of another article for use with apparatus for heating smokable material to volatilise at least one component of the smokable material.

Referring to FIG. 7, there is shown a schematic cross-sectional view of an example of an article according to another embodiment of the invention. The article 4 is for use with apparatus for heating smokable material to volatilise at least one component of the smokable material, such as the apparatus 200 of the system 2000 shown in FIG. 14 and described below.

The article 4 comprises a carrier 10 having a surface and smokable material 20 on the surface of the carrier 10. In this embodiment, the surface is a major surface of the carrier 10. The smokable material 20 is in the form of a gel or thin film.

In this embodiment, the carrier 10 is a sheet of aluminium. The aluminium, and thus the carrier 10, has a thermal conductivity of at least 200 W/(m·K), such as about 237 W/(m·K). Accordingly, in use the carrier 10 transfers heat energy to the smokable material 20 from the side of the carrier 10 opposite to that on which the smokable material 20 is located.

In this embodiment, the smokable material 20 is coextensive or substantially coextensive with the surface of the carrier 10. That is, the smokable material 20 covers all, or substantially all, of the surface of the carrier 10. In other embodiments, this may not be true. For example, in some embodiments, the smokable material 20 covers a majority of the surface of the carrier 10. In other embodiments, the smokable material 20 comprises plural discrete quantities of the smokable material on the surface of the carrier 10.

Figure 8:
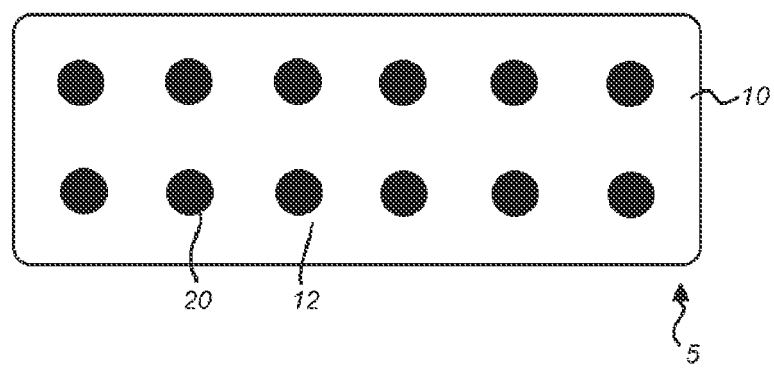
FIG. 8 shows a schematic plan view of an example of another article for use with apparatus for heating smokable material to volatilise at least one component of the smokable material.
Figure 9:
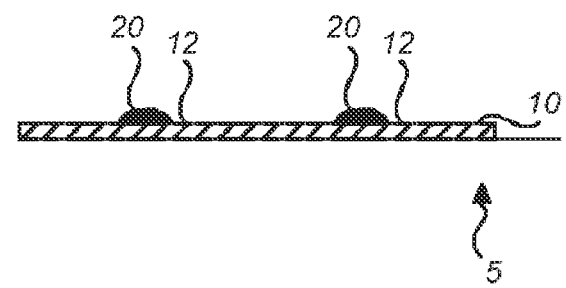
FIG. 9 shows a schematic cross-sectional view of the article of FIG. 8.

For example, referring to FIGS. 8 and 9, there are shown schematic plan and cross-sectional views of an example of an article according to another embodiment of the invention. The article 5 is for use with apparatus for heating smokable material to volatilise at least one component of the smokable material, such as the apparatus 200 of the system 2000 shown in FIG. 14 and described below.

In this embodiment, the article 5 is identical to the article 4 of FIG. 7, except for the form of the smokable material 20. In this embodiment, the smokable material 20 comprises plural discrete quantities of the smokable material 20 on the surface of the carrier 10. The carrier 10 comprises plural thermally-conductive portions 12 on which the respective discrete quantities of smokable material 20 are located.

During use either of the article 4 of FIG. 7 or the article 5 of FIGS. 8 and 9, heat energy may be applied to the carrier 10 (or one of the thermally-conductive portions 12 of the carrier 10) on a side of the carrier 10 opposite to that on which the smokable material 20 is located. When this happens, the heat energy is conducted by the carrier 10 (or thermally-conductive portions 12) to the smokable material 20. As a result, at least one component of the smokable material 20 (or a discrete quantity of the smokable material 20) may be volatilised for inhalation by a user.

Figure 10:
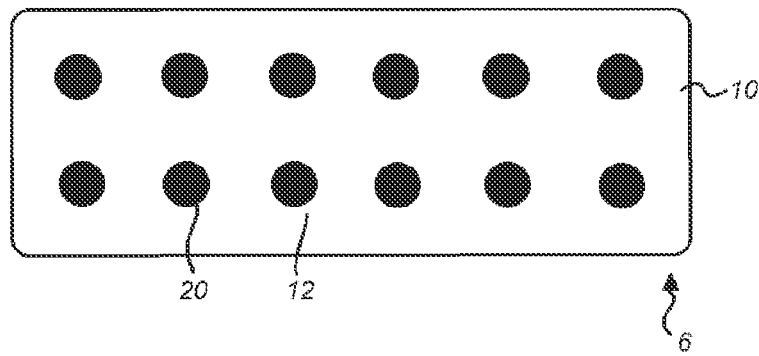
FIG. 10 shows a schematic plan view of an example of another article for use with apparatus for heating smokable material to volatilise at least one component of the smokable material.
Figure 11:
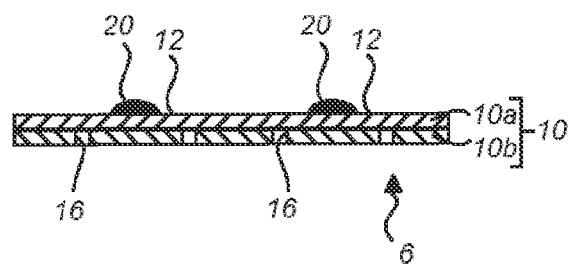
FIG. 11 shows a schematic cross-sectional view of the article of FIG. 10.

Referring to FIGS. 10 and 11, there are shown schematic plan and cross-sectional views of an example of an article according to another embodiment of the invention. The article 6 is for use with apparatus for heating smokable material to volatilise at least one component of the smokable material, such as the apparatus 100 shown in FIG. 13 and described below.

In this embodiment, the article 6 is identical to the article 1 of FIGS. 1 and 2, except for the form of the carrier 10. In this embodiment, the carrier 10 comprises a laminate. The laminate comprises a layer of nickel 10b and a layer of aluminium 10a. The layer of aluminium 10a is located between the layer of nickel 10b and the smokable material 20. In this embodiment, the smokable material 20 is in contact with the layer of aluminium 10a. In other embodiments, the positions of the layer of aluminium and layer of nickel may be reversed, so that the layer of nickel is located between the layer of aluminium and the smokable material 20. In some such embodiments, the smokable material 20 may be in contact with the layer of nickel.

As for the article 1 of FIGS. 1 and 2, the carrier 10 has plural thermally-conductive portions 12 on which the respective discrete quantities of smokable material 20 are located. The article 6 is configured so that one of the discrete quantities of smokable material 20 is heatable in use while inhibiting heating of another of the discrete quantities of smokable material 20. More specifically, between the portions 12 of the carrier 10, and as compared to the portions 12 of the carrier 10, the carrier 10 is shaped to form thermal barriers 14 for inhibiting heat conduction from one of the portions 12 of the carrier 10 towards another of the portions 12 of the carrier 10 in use.

In this embodiment, each of the thermal barriers 14 comprises a plurality of spaced-apart through holes or perforations 16 through the layer of nickel 10b. As for the article 1 of FIGS. 1 and 2, the effect of the through holes or perforations 16 is to reduce the cross-sectional area of the carrier 10 at the thermal barrier 14, which impairs heat conduction across the thermal barrier 14. The perforations 16 through the layer of nickel 10b are the same in number and arrangement as the perforations through the carrier 10 of the article 1 of FIGS. 1 and 2. However, in other embodiments, modifications to the path on which the perforations lie, and/or the shape and/or number of the perforations 16 may be varied as discussed above in relation to article 1.

Figure 12:
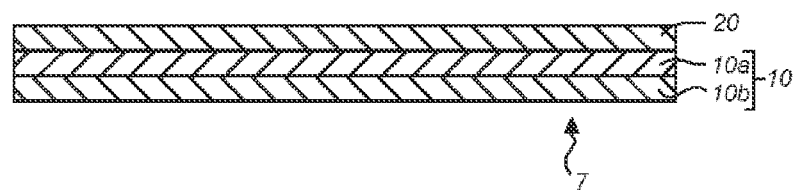
FIG. 12 shows a schematic cross-sectional view of an example of another article for use with apparatus for heating smokable material to volatilise at least one component of the smokable material.

Referring to FIG. 12, there is shown a schematic cross-sectional view of an example of an article according to another embodiment of the invention. The article 7 is for use with apparatus for heating smokable material to volatilise at least one component of the smokable material, such as the apparatus 200 of the system 2000 shown in FIG. 14 and described below.

In this embodiment, the article 7 is identical to the article 4 of FIG. 7, except for the form of the carrier 10. In this embodiment, the carrier 10 comprises a laminate. The laminate comprises a layer of nickel 10b and a layer of paper 10a. The layer of paper 10a is located between the layer of nickel 10b and the smokable material 20. In this embodiment, the smokable material 20 is in contact with the layer of paper 10a. The layer of paper 10a aids fixing of the smokable material 20 relative to the layer of nickel 10b. Portions of the layer of nickel 10b are heatable inductively, and the layer of paper 10a has a thickness that permits sufficient heat energy to pass from the layer of nickel 10b to the smokable material 20 in use, to thereby cause at least one component of the smokable material 20 to be volatilised for inhalation by a user.

In each of the articles 1, 2, 3, 6 shown in FIGS. 1 to 6 and FIGS. 10 and 11, the carrier 10 comprises heating material that is heatable by penetration with a varying magnetic field. There will now be described an apparatus 100 with which these articles 1, 2, 3, 6 are usable, and which comprises magnetic field generators for generating varying magnetic fields for penetrating the respective thermally-conductive portions 12 of the carrier 10 in use.

Figure 13:
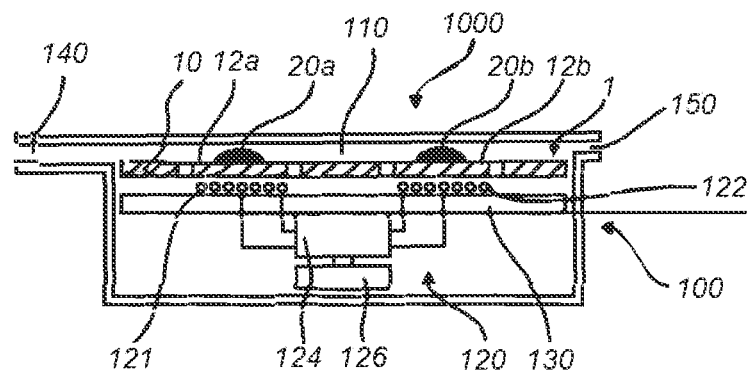
FIG. 13 shows a schematic cross-sectional view of an example of a system comprising the article of FIGS. 1 and 2, and apparatus for heating the smokable material of the article to volatilise at least one component of the smokable material.

Referring to FIG. 13, there is shown a schematic cross-sectional view of an example of a system according to an embodiment of the invention. The system 1000 comprises an apparatus 100 and the article 1 of FIGS. 1 and 2. The apparatus 100 is for heating the smokable material 20 of the article 1 to volatilise at least one component of the smokable material 20. In the interest of conciseness, the article 1 will not be described again in detail. Any of the herein-described possible variations to the article 1 of FIGS. 1 and 2 may be made to the article 1 of the system 1000 of FIG. 13 to form separate respective embodiments of a system. Similarly, the article 1 of FIGS. 1 and 2 may be replaced in the system 1000 by one of the articles 2, 3, 6 shown in FIGS. 3 to 6, 10 and 11 to form separate respective embodiments of a system.

The apparatus 100 comprises a heating zone 110 for receiving at least a portion of the article 1, and a heating device 120 for heating the thermally-conductive portions 12 of the carrier 10 of the article 1 when the article 1 is located in the heating zone 110.

In this embodiment, the heating zone 110 comprises a recess for receiving the article 1. The article 1 may be insertable into the heating zone 110 by a user in any suitable manner, such as through a slot in a wall of the apparatus 100, or by first moving a portion of the apparatus, such as the mouthpiece discussed below, to access to the heating zone 110. In other embodiments, the heating zone 110 may be other than a recess, such as a shelf, a surface, or a projection, and may require mechanical mating with the article 1 in order to co-operate with, or receive, the article 1. In this embodiment, the heating zone 110 is sized and shaped to accommodate the whole article 1. In other embodiments, the heating zone 110 may be dimensioned to receive only a portion of the article in use.

The apparatus 100 has an outlet 140 for permitting volatilised components of the smokable material 20 to pass from the heating zone 110 to an exterior of the apparatus 100 when the smokable material 20 is heated in the heating zone 110 in use. In this embodiment, the outlet 140 is in the form of a mouthpiece for insertion into a user's mouth. The apparatus 100 also has an air inlet 150 that fluidly connects the heating zone 110 with the exterior of the apparatus 100. In use, a user is able to inhale the volatilised component(s) of the smokable material 20 by drawing the volatilised component(s) through the outlet 140. As the volatilised component(s) is/are removed from the heating zone 110, air may be drawn into the heating zone 110 via the air inlet 150.

The heating device 120 comprises plural heaters 121, 122 for heating respective ones of the thermally-conductive portions 12a, 12b of the carrier 10 of the article 1 in use. As noted above with reference to FIGS. 1 and 2, the thermally-conductive portions 12a, 12b of the carrier 10 are made of heating material that is heatable by penetration with respective varying magnetic fields. In this embodiment, the heaters 121, 122 comprise respective magnetic field generators 121, 122 for generating the varying (such as alternating) magnetic fields for penetrating the respective thermally-conductive portions 12a, 12b in use. More specifically, the magnetic field generators 121, 122 comprise respective coils 121, 122.

The coils 121, 122 may take any suitable form. In this embodiment, each of the coils 121, 122 comprises a flat coil of electrically-conductive material, such as copper. That is, the coils are two-dimensional spirals. The coils are substantially circular in this embodiment, but in other embodiments they may take a different shape, such as generally square. In other embodiments, the coils may take a still different form, such as helical coils of electrically-conductive material.

The apparatus 100 of this embodiment comprises a printed circuit board 130, on or in which the coils 121, 122 are located. The coils may be printed on the printed circuit board 130. This arrangement may be relatively low cost, allows for many coils to be integrated within a single printed circuit board and/or with drive electronics to form a single solid state device that may make efficient use of space, and may be open to mass production such as using manufacturing lines already set up for the manufacture of passive printed circuit boards. Further, such an arrangement has been found to show very good reproducibility in properties (e.g. complex and real impedance).

The apparatus 100 of this embodiment also comprises a controller 124 for controlling operation of the heaters 121, 122. The apparatus further comprises an electrical power source 126 that is connected to the controller 124. In use, the controller 124 may cause a varying electrical current, such as an alternating current, to pass from the electrical power source 126 through the coils 121, 122, thereby to cause the coils to generate the respective varying magnetic fields.

In this embodiment, the controller 124 comprises an integrated circuit (IC), such as an IC on a printed circuit board (PCB). In other embodiments, the controller 124 may take a different form. The controller 124 is operated in this embodiment by user-operation of a user interface (not shown) of the apparatus 100. The user interface 118 may comprise a push-button, a toggle switch, a dial, a touchscreen, or the like.

The electrical power source 126 of this embodiment is a rechargeable battery. In other embodiments, the electrical power source 126 may be other than a rechargeable battery, such as a non-rechargeable battery, a capacitor, a battery-capacitor hybrid, or a connection to a mains electricity supply.

Accordingly, when the article 1 is located in the heating zone 110 in use, operation of the user interface by a user causes the controller 124 to cause an alternating electrical current to pass through each of the coils 121, 122, so as to cause the coils 121, 22 to generate respective alternating magnetic fields. The coils 121, 122 and the thermally-conductive portions 12a, 12b of the carrier 10 of the article 1 are suitably relatively positioned so that the varying magnetic fields produced by the coils 121, 122 penetrate the respective thermally-conductive portions 12a, 12b of the carrier 10 of the article 1. When the heating material of the portions 12a, 12b of the carrier 10 is an electrically-conductive material, as in this embodiment, this causes the generation of one or more eddy currents in the heating material. The flow of eddy currents in the heating material against the electrical resistance of the heating material causes the heating material to be heated by Joule heating. Further, when the heating material is made of a magnetic material, as in this embodiment, the orientation of magnetic dipoles in the heating material changes with the changing applied magnetic field, which causes heat to be generated in the heating material.

The controller 124 of this embodiment is for controlling operation of at least one of the heaters 121, 122 independently of at least one other of the heaters 121, 122. Therefore, for example, the controller 124 may control a first of the heaters 121, 122 to inductively heat a first 12a of the thermally-conductive portions 12 of the carrier 10. This initiates volatilisation of at least one component of the smokable material 20a on that first portion 12a of the carrier 10 and formation of an aerosol therein. Over time, the controller 124 may control a second of the heaters 122 to inductively heat a second 12b of the thermally-conductive portions 12 of the carrier 10. This initiates volatilisation of at least one component of the smokable material 20b on that second portion 12b of the carrier 10 and formation of an aerosol therein. Accordingly, there is provided progressive heating of the article 1, and thus the smokable material 20 of the article 1, over time.

In this embodiment, the first heater 121 and the first thermally-conductive portion 12a of the carrier 10 are closer to the outlet 140 than the second heater 122 and the second thermally-conductive portion 12b of the carrier 10. This helps to enable an aerosol to be formed and released relatively rapidly from the article 1 at a location relatively close to the outlet 140, for inhalation by a user, yet provides time-dependent release of aerosol, so that aerosol continues to be formed and released even after the smokable material 20 on the first portion 12a of the carrier 10 has ceased generating aerosol. Such cessation of aerosol generation may occur as a result of the smokable material 20 on the first portion 12a of the carrier 10 becoming exhausted of volatilisable components of the smokable material 20.

The apparatus 100 may comprise a temperature sensor (not shown) for sensing a temperature of the heating zone 110 or of the article 1. The temperature sensor may be communicatively connected to the controller 124, so that the controller 124 is able to monitor the temperature. On the basis of one or more signals received from the temperature sensor, the controller 124 may adjust a characteristic of the varying or alternating electrical current passed through the coils 121, 122 as necessary, in order to ensure that the temperature of the smokable material 20 remains within a predetermined temperature range. The characteristic may be, for example, amplitude or frequency or duty cycle.

Within the predetermined temperature range, in use the smokable material 20 is heated sufficiently to volatilise at least one component of the smokable material 20 without combusting the smokable material 20. Accordingly, the controller 124, and the apparatus 100 as a whole, is arranged to heat the smokable material 20 to volatilise the at least one component of the smokable material 20 without combusting the smokable material 20. In some embodiments, the temperature range is about 50° C. to about 350° C., such as between about 50° C. and about 250° C., between about 50° C. and about 150° C., between about 50° C. and about 120° C., between about 50° C. and about 100° C., between about 50° C. and about 80° C., or between about 60° C. and about 70° C. In some embodiments, the temperature range is between about 170° C. and about 220° C. In other embodiments, the temperature range may be other than this range. In some embodiments, the upper limit of the temperature range could be greater than 300° C. In some embodiments, the temperature sensor may be omitted. In some embodiments, the heating material may have a Curie point temperature selected on the basis of the maximum temperature to which it is desired to heat the heating material, so that further heating above that temperature by induction heating the heating material is hindered or prevented.

Figure 14:
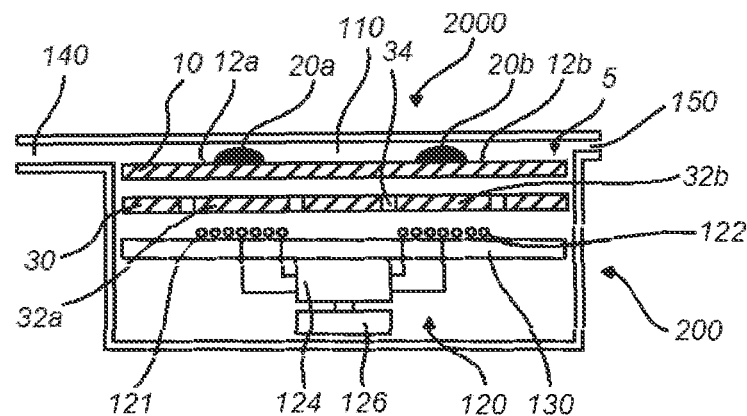
FIG. 14 shows a schematic cross-sectional view of an example of another system comprising an article comprising smokable material, and apparatus for heating the smokable material of the article to volatilise at least one component of the smokable material.

Referring to FIG. 14 there is shown a schematic cross-sectional view of an example of another system according to an embodiment of the invention. The system 2000 comprises an apparatus 200 and the article 5 of FIGS. 8 and 9. The apparatus 200 is for heating the smokable material 20 of the article 5 to volatilise at least one component of the smokable material 20. In the interest of conciseness, the article 5 will not be described again in detail. Any of the herein-described possible variations to the article 5 of FIGS. 8 and 9 may be made to the article 5 of the system 2000 of FIG. 14 to form separate respective embodiments of a system. Similarly, the article 5 of FIGS. 8 and 9 may be replaced in the system 2000 by one of the articles 4, 7 shown in FIGS. 7 and 12 to form separate respective embodiments of a system.

The apparatus 200 of FIG. 14 is identical to the apparatus 100 of the system 1000 of FIG. 13 except that, whereas the apparatus 100 is arranged to heat the thermally-conductive portions 12a, 12b of the carrier 10 of the article 1 inductively by penetrating the thermally-conductive portions 12 with the varying (e.g. alternating) magnetic field, the apparatus 200 of FIG. 14 heats the thermally-conductive portions 12 of the carrier 10 of the article 5 by heat conduction. That is, in the system 2000 of FIG. 14, the apparatus 200 applies heat energy to the thermally-conductive portions 12a, 12b of the article 5 to heat the smokable material 20.

The apparatus 200 comprises a heating zone 110 for receiving at least a portion of the article 5, and a substrate 30 comprising plural thermally-conductive portions 32a, 32b. Between the portions 32a, 32b of the substrate 30, the substrate 30 is shaped to create a thermal barrier 34 for inhibiting heat conduction from one of the portions 32a, 32b of the substrate 30 towards another of the thermally-conductive portions 32a, 32b of the substrate 30 in use. In this embodiment, the substrate 30 is shaped to form the thermal barrier 34 between the portions 32a, 32b of the substrate 30 and as compared to the portions 32a, 32b of the substrate 30. Each of the thermally-conductive portions 32a, 32b of the substrate 30 is made from heating material that is heatable by penetration with a varying magnetic field. In this embodiment, the substrate 30 (and thus the thermally-conductive portions 32a, 32b of the substrate 30) comprises steel that is nickel-coated to help prevent corrosion. In other embodiments, the substrate 30 (and thus the thermally-conductive portions 32a, 32b of the substrate 30) comprises aluminium. The aluminium may be nickel-coated, again to help prevent corrosion.

In this embodiment, the substrate 30 comprises twelve thermally-conductive portions 32a, 32b, and the substrate 30 is shaped to form thermal barriers 34 between respective pairs of the portions 32a, 32b of the substrate 30. More specifically, the substrate 30 is shaped to form plural thermal barriers 34 that surround respective ones of the thermally-conductive portions 32a, 32b of the substrate 30. Therefore, any specific one or plurality of the portions 32a, 32b is heatable in use without, or without significant, heating of any of the other portions 32a, 32b of the substrate 30.

In this embodiment, the twelve thermally-conductive portions 32a, 32b of the substrate 30 are arranged in two rows of six. The thermally-conductive portions 32a, 32b are therefore arranged as a two-dimensional array. In other embodiments, the substrate 30 may comprise more or fewer thermally-conductive portions 32a, 32b, and in some embodiments, the portions 32a, 32b may be arranged as a one-dimensional array, for example. That is, all of the thermally-conductive portions 32a, 32b of the substrate 30 may be relatively aligned in a single row, which may be a straight or linear row.

In this embodiment, each of the thermal barriers 34 in the substrate 30 comprises a plurality of spaced-apart through holes or perforations through the substrate 30. The effect of the through holes or perforations is to reduce the cross-sectional area of the substrate 30 at the thermal barrier 34, which impairs heat conduction across the thermal barrier 34. The presence of air in the through holes or perforations may also contribute to the thermal insulation properties. The perforations of each thermal barrier 34 are arranged on a circular path that surrounds one of the thermally-conductive portions 32a, 32b of the substrate 30. However, in other embodiments, the path may be other than circular, such as polygonal or elliptical. In this embodiment, each of the perforations is itself circular. However, in other embodiments, one or more of the perforations of a thermal barrier 34 may be other than circular, such as polygonal, elliptical or elongate or slot-shaped.

In this embodiment, each thermal barrier 34 comprises eight through holes or perforations through the substrate 30. That is, there is a total of eight holes on the path. However, in other embodiments, one or each of the thermal barriers 34 may comprise more through holes or perforations through the substrate 30, such as between twenty and thirty holes. In some embodiments, one or each of the thermal barriers 34 may comprise fewer holes through the substrate 30. For example, in some embodiments, the thermal barrier 34 may comprise or consist of only one or two holes through the substrate 30. In such embodiment, the through hole(s) may be elongate or slot-shaped in the plane of the substrate 30, so as to sufficiently resist the conduction of heat across the thermal barrier 34.

The perforations may be formed by laser etching the substrate 30, by punching the substrate 30, or by any other suitable method.

In some variations to this embodiment, the, or each, thermal barrier 34 of the substrate 30 may comprise one or more channels or blind holes in the substrate 30. The one or more channels or blind holes may be provided in addition to, or instead of, the through hole(s) or perforations discussed above.

The apparatus 200 also comprises a heating device 120 for heating one or a subset of the thermally-conductive portions 32a, 32b of the substrate 30 to thereby heat portions of the heating zone 110. The heating device 120 of the apparatus 200 of FIG. 14 is the same as the heating device 120 of the apparatus 100 of FIG. 13. However, rather than being arranged to inductively heat thermally-conductive portions of the article 5 located in the heating zone 110, the heating device 120 of the apparatus 200 of FIG. 14 is used to inductively heat the thermally-conductive portions 32a, 32b of the substrate 30 of the apparatus 200. That is, the plural heaters 121, 122 comprise respective magnetic field generators for generating varying magnetic fields for penetrating the respective thermally-conductive portions 32a, 32b of the substrate 30 in use. The heat generated in the thermally-conductive portions 32a, 32b of the substrate 30 passes to the article 5 in the heating zone 110 by way of heat conduction.

Accordingly, the carrier 10 of the article 5 with which the apparatus 200 is usable need not be made of a material that is readily inductively heatable to heat the smokable material 20 to a temperature sufficient to volatilise at least one component of the smokable material 20. This may enable the carrier 10 to be made of cheaper or more readily-available material.

Similarly to the controller 124 of the apparatus 100, the controller 124 of the apparatus 200 is for controlling operation of at least one of the plural heaters 121, 122 independently of at least one other of the plural heaters 121, 122. Thus, the apparatus 200 is usable to provide progressive heating of the article 5, and thus the smokable material 20 of the article 5, over time in a manner similar to the apparatus 100 of FIG. 13.

For example, the controller 124 may control a first of the heaters 121, 122 to inductively heat a first 32a of the thermally-conductive portions 32 of the substrate 30. This in turn causes a first thermally-conductive portion 12a of the carrier 10 of the article 5 adjacent the first thermally-conductive portion 32a of the substrate 30 to be heated by heat conduction. This initiates volatilisation of at least one component of the smokable material 20a on that first portion 12a of the carrier 10 and formation of an aerosol therein. Over time, the controller 124 may control a second of the heaters 122 to inductively heat a second 32b of the thermally-conductive portions 32 of the substrate 30. This in turn causes a second thermally-conductive portion 12b of the carrier 10 of the article 5 adjacent the second thermally-conductive portion 32b of the substrate 30 to be heated by heat conduction. This initiates volatilisation of at least one component of the smokable material 20b on that second portion 12b of the carrier 10 and formation of an aerosol therein.

The article 5 of FIGS. 8 and 9 may be replaced in the system 2000 by one of the articles 1, 2, 3, 6 shown in FIGS. 1 to 6 and FIGS. 10 and 11 to form separate respective embodiments of a system. In such systems, the article and the apparatus 200 may be relatively arrange so that the thermally-conductive portions 12 of the carrier 10 of the article 1, 2, 3, 6 align with the thermally-conductive portions 32a, 32b of the substrate 30 of the apparatus 200 when the article 1, 2, 3, 6 is in the heating zone 110.

In some embodiments, the apparatus 100, 200 is sold, supplied or otherwise provided separately from the article 1, 2, 3, 4, 5, 6 with which the apparatus 100, 200 is usable.

However, in some embodiments, the apparatus 100, 200 and one or more of the articles 1, 2, 3, 4, 5, 6 may be provided together as a system, such as a kit or an assembly, possibly with additional components, such as cleaning utensils.

In each of the above described embodiments, the article 1, 2, 3, 4, 5, 6 is a consumable article. Once all, or substantially all, of the volatilisable component(s) of the smokable material 20 in the article 1, 2, 3, 4, 5, 6 has/have been spent, the user may remove the article 1, 2, 3, 4, 5, 6 from the apparatus 100, 200 and dispose of the article 1, 2, 3, 4, 5, 6. The user may subsequently re-use the apparatus 100, 200 with another of the articles 1, 2, 3, 4, 5, 6. However, in other respective embodiments, the article may be non-consumable, and the apparatus and the article may be disposed of together once the volatilisable component(s) of the smokable material has/have been spent.

Figure 15:
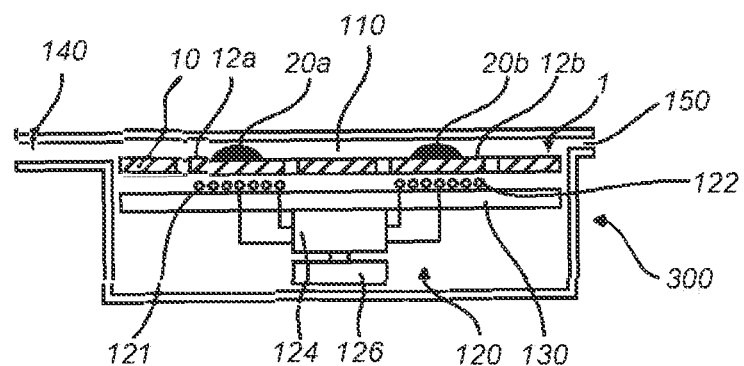
FIG. 15 shows a schematic cross-sectional view of an example of apparatus for heating smokable material to volatilise at least one component of the smokable material, the apparatus including as an integral part the article of FIGS. 1 and 2.

For example, referring to FIG. 15, there is shown a schematic cross-sectional view of an example of another apparatus according to an embodiment of the invention. The apparatus 300 itself comprises the article 1 of FIGS. 1 and 2, and the apparatus 300 is for heating the smokable material 20 of the article 1 to volatilise at least one component of the smokable material 20. In the interest of conciseness, the article 1 will not be described again in detail. Any of the herein-described possible variations to the article 1 of FIGS. 1 and 2 may be made to the article 1 of the apparatus 300 of FIG. 15 to form separate respective embodiments of an apparatus. Similarly, the article 1 of FIGS. 1 and 2 may be replaced in the apparatus 300 by one of the articles 2, 3, 6 shown in FIGS. 3 to 6, 10 and 11 to form separate respective embodiments of an apparatus.

The apparatus 300 of FIG. 15 is identical to the apparatus 100 of the system 1000 of FIG. 13 except that, whereas the apparatus 100 is arranged for the article 1 to be insertable into the heating zone 110 by a user, in the apparatus 300 of FIG. 15 the article 1 is not insertable into the heating zone 110 by a user. That is, in the apparatus 300 of FIG. 15, the article 1 is an integral part of the apparatus 300. Accordingly, in use, the heating device 120 of the apparatus 300 is used to inductively heat the thermally-conductive portions 12a, 12b of the carrier 10 of the article 1, thereby to volatilise at least one component of the smokable material 20a, 20b on the thermally-conductive portions 12a, 12b of the carrier 10 and form an aerosol therein. The controller 124 of the apparatus 300 may effect progressive heating of the article 1, and thus the smokable material 20 of the article 1, over time in a manner corresponding to that described above. The apparatus 300 may be used so that aerosol continues to be formed and released over time, until for example the smokable material 20a, 20b becomes exhausted of volatilisable components of the smokable material.

In each of the embodiments discussed above the heating material is steel. However, in other embodiments, the heating material may comprise one or more materials selected from the group consisting of: an electrically-conductive material, a magnetic material, and a magnetic electrically-conductive material. In some embodiments, the heating material may comprise a metal or a metal alloy. In some embodiments, the heating material may comprise one or more materials selected from the group consisting of: aluminium, gold, iron, nickel, cobalt, conductive carbon, graphite, plain-carbon steel, stainless steel, ferritic stainless steel, copper, and bronze. Other heating material(s) may be used in other embodiments. It has been found that, when magnetic electrically-conductive material is used as the heating material, magnetic coupling between the magnetic electrically-conductive material and an electromagnet of the apparatus in use may be enhanced. In addition to potentially enabling magnetic hysteresis heating, this can result in greater or improved Joule heating of the heating material, and thus greater or improved heating of the smokable material.

The heating material may have a skin depth, which is an exterior zone within which most of an induced electrical current and/or induced reorientation of magnetic dipoles occurs. By providing that the heating material has a relatively small thickness, a greater proportion of the heating material may be heatable by a given varying magnetic field, as compared to heating material having a depth or thickness that is relatively large as compared to the other dimensions of the heating material. Thus, a more efficient use of material is achieved and, in turn, costs are reduced.

In many of the above-described embodiments, the thermally-conductive portion(s) 12, 32 of the carrier 10 or substrate 30 are heated inductively by penetrating the thermally-conductive portion(s) 12, 32 with a varying (e.g. alternating) magnetic field. In other embodiments, the heating device 120 of the apparatus 100, 200, 300 may be free from an induction heater. In some such embodiments, the electrical energy in the heaters 121, 122 may be converted straight into heat energy for heating the thermally-conductive portion(s) 12, 32 of the carrier 10 or substrate 30. That is, the heaters 121, 122 may heat up so that the thermally-conductive portion(s) 12, 32 of the carrier 10 or substrate 30 are heated by a process that involves heat conduction only, in place of induction.

As noted above, the portion(s) 12, 32 of the carrier 10 or substrate 30 are thermally-conductive. To ensure that these portions are sufficiently thermally-conductive, the carrier 10 or substrate 30 preferably has, or comprises, a material having a thermal conductivity of at least 10 W/(m·K). More preferably, the thermal conductivity is at least 90 W/(m·K). Still more preferably, the thermal conductivity is at least 200 W/(m·K). Example materials and associated thermal conductivities for the carrier 10 and/or substrate 30 are: silver (429 W/(m·K)), copper (401 W/(m·K)), gold (310 W/(m·K)), brass (109 W/(m·K)), nickel (91 W/(m·K)), platinum (70 W/(m·K)), cast iron (55 W/(m·K)), carbon steel (max 0.5% carbon) (54 W/(m·K)), and carbon steel (max 1.5% carbon) (36 W/(m·K)). The better a thermally-conductive portion 12, 32 is at conducting heat, the more readily the heat may spread out within the portion 12, 32, which may help increase the uniformity of heating of the portion 12, 32 in use. However, if the thermally-conductive portion 12, 32 is relatively less thermally-conductive, relative uniformity of heating of the portion 12, 32 may still be achieved through use of the flat coil(s) described herein to cause the heating inductively. That is, if the heat source is in the form of a flat uniform plate, as it tends to be for a flat coil, then the thermal-conductivity of the portion 12, 32 tends to be less important.

In each of the above described embodiments, the smokable material comprises tobacco. However, in respective variations to each of these embodiments, the smokable material may consist of tobacco, may consist substantially entirely of tobacco, may comprise tobacco and smokable material other than tobacco, may comprise smokable material other than tobacco, or may be free from tobacco. In some embodiments, the smokable material may comprise a vapour or aerosol forming agent or a humectant, such as glycerol, propylene glycol, triacetin, or diethylene glycol.

In each of the above described embodiments, the smokable material is in the form of a gel or thin film. However, in other embodiments, the smokable material may be in a different form. For example, the smokable material may take the form of a liquid or a non-liquid, such as a solid.

In order to address various issues and advance the art, the entirety of this disclosure shows by way of illustration and example various embodiments in which the claimed invention may be practised and which provide for superior articles for use with apparatus for heating smokable material to volatilise at least one component of the smokable material, superior apparatus for heating smokable material to volatilise at least one component of the smokable material, and superior systems comprising such an article and such apparatus. The advantages and features of the disclosure are of a representative sample of embodiments only, and are not exhaustive and/or exclusive. They are presented only to assist in understanding and teach the claimed and otherwise disclosed features. It is to be understood that advantages, embodiments, examples, functions, features, structures and/or other aspects of the disclosure are not to be considered limitations on the disclosure as defined by the claims or limitations on equivalents to the claims, and that other embodiments may be utilised and modifications may be made without departing from the scope and/or spirit of the disclosure. Various embodiments may suitably comprise, consist of, or consist in essence of, various combinations of the disclosed elements, components, features, parts, steps, means, etc. The disclosure may include other inventions not presently claimed, but which may be claimed in future.

The invention claimed is:

1. An article for use with an apparatus for heating smokable material to volatilize at least one component of the smokable material, the article comprising:
   a carrier having a surface, the carrier having plural thermally-conductive portions; and
   smokable material on the surface of the carrier,
   wherein at least one of perforations, through holes, channels and blind holes is formed in the surface of the carrier between respective pairs of the plural thermally-conductive portions of the carrier.

2. The article of claim 1, wherein the smokable material is coextensive with the surface of the carrier.

3. The article of claim 1, wherein the smokable material comprises plural discrete quantities of the smokable material on the surface of the carrier.

4. The article of claim 1, wherein the carrier is a sheet.

5. The article of claim 1, wherein the carrier has, or comprises a material having, a thermal conductivity of at least 10 W/(m·K).

6. The article of claim 1, wherein the carrier comprises at least one of nickel or aluminum.

* * * * *